(12) United States Patent
Zhao et al.

(10) Patent No.: US 7,570,354 B1
(45) Date of Patent: Aug. 4, 2009

(54) IMAGE INTENSIFICATION FOR LOW LIGHT INSPECTION

(75) Inventors: Wei Zhao, Sunnyvale, CA (US); Stuart L. Friedman, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 177 days.

(21) Appl. No.: 11/876,009

(22) Filed: Oct. 22, 2007

Related U.S. Application Data

(60) Provisional application No. 60/970,320, filed on Sep. 6, 2007.

(51) Int. Cl.
*G01N 21/88* (2006.01)
(52) U.S. Cl. ............... 356/237.2; 356/237.4; 356/237.5
(58) Field of Classification Search ............ 356/237.1, 356/237.2, 237.3, 237.4, 237.5, 237.6, 394
See application file for complete search history.

(56) References Cited

U.S. PATENT DOCUMENTS 7,339,661 B2 * 3/2008 Korngut et al. .......... 356/237.2

* cited by examiner

*Primary Examiner*—Kiet T Nguyen
(74) *Attorney, Agent, or Firm*—Luedeka, Neely & Graham, P.C.

(57) ABSTRACT

An optical inspection system for inspecting a substrate. A beam source produces a light beam and directs it toward a surface of the substrate, thereby producing a reflected light beam that is received by an intensifier module. A photocathode receives the reflected light beam at a first surface and producing a shower of photoelectrons at a second opposing surface. An electrical field receives the shower of photoelectrons and accelerates the photoelectrons away from the second surface of the photocathode, thereby producing an enhanced output. A sensor receives the enhanced output from the intensifier module and produces electrical signals in response to the enhanced output. A controller receives the electrical signals and produces images of the substrate, based at least in part on the electrical signals. The controller also controls and coordinates the operation of the beam source, the intensifier module, and the sensor.

18 Claims, 3 Drawing Sheets

IMAGE INTENSIFICATION FOR LOW LIGHT INSPECTION

This application claims all priorities and other benefits of prior pending U.S. provisional application 60/970,320, filed 2007 Sep. 6.

FIELD

This invention relates to the field of integrated circuit fabrication. More particularly, this invention relates to optical signal enhancement.

BACKGROUND

Because of the high complexity of modern integrated circuits, and the delicacy of the processes by which they are formed, they are traditionally inspected at many different times during fabrication. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

As used in the art, the term "inspection" is typically limited to optical inspection of the integrated circuits, rather than an electrical "inspection," which is typically referred to as "testing." Inspection is also performed on other types of items that are used in the integrated circuit fabrication process, such as masks and reticles. As used herein, the term "substrate" applies without limitation to integrated circuits, the wafers on which they are formed, masks, and reticles.

Because feature size continues to drop, optical inspection becomes increasingly harder to perform. One challenge is to provide a sufficient amount of light at a wavelength that is necessary to resolve the small features to be inspected. If there is an insufficient amount of light provided, then sensor noise tends to limit the performance of the inspection system. This is generally referred to as having an excessively low signal to noise ratio, where the optical signal that is produced is too low in comparison to the optical and electrical noise inherent in the inspection system.

What is needed, therefore, is a system that overcomes problems such as those described above, at least in part.

SUMMARY

The above and other needs are met by an optical inspection system for inspecting a substrate. A beam source produces a light beam and directs it toward a surface of the substrate, thereby producing a reflected light beam that is received by an intensifier module with or without an imaging system. A photocathode receives the reflected light beam at a first surface and produces a shower of photoelectrons at a second opposing surface. An electrical field receives the shower of photoelectrons and accelerates the photoelectrons away from the second surface of the photocathode, thereby producing an enhanced output. A sensor receives the enhanced output from the intensifier module and produces electrical signals in response to the enhanced output. A controller receives the electrical signals and produces images of the substrate, based at least in part on the electrical signals. The controller also controls and coordinates the operation of the beam source, the intensifier module, and the sensor.

In this manner, the relatively weak optical signal that is received by the intensifier module is enhanced before delivery to the sensor, and the optical inspection system is able to provide an image having a higher signal to noise ratio than an optical inspection system without the intensifier module.

In various embodiments, the intensifier module includes a scintillator for receiving the shower of photoelectrons at a first surface and producing photons at a second opposing surface, where the photons are the enhanced output of the intensifier module. In some embodiments the intensifier module includes at least one magnetic focusing tube for receiving the shower of photoelectrons and producing a spatially enhanced shower of photoelectrons, where the spatially enhanced photoelectrons are the enhanced output of the intensifier module. In some embodiments the intensifier module includes a magnetic field for receiving the shower of photoelectrons and producing a spatially enhanced shower of photoelectrons, where the spatially enhanced photoelectrons are the enhanced output of the intensifier module.

In some embodiments the intensifier module includes a fiber optic plate for coupling the enhanced output of the intensifier module to the sensor. In some embodiments the intensifier module includes a relay lens for coupling the enhanced output of the intensifier module to the sensor. In some embodiments the sensor includes at least one of a charge coupled device, a CMOS device, and a time delay and integration device.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
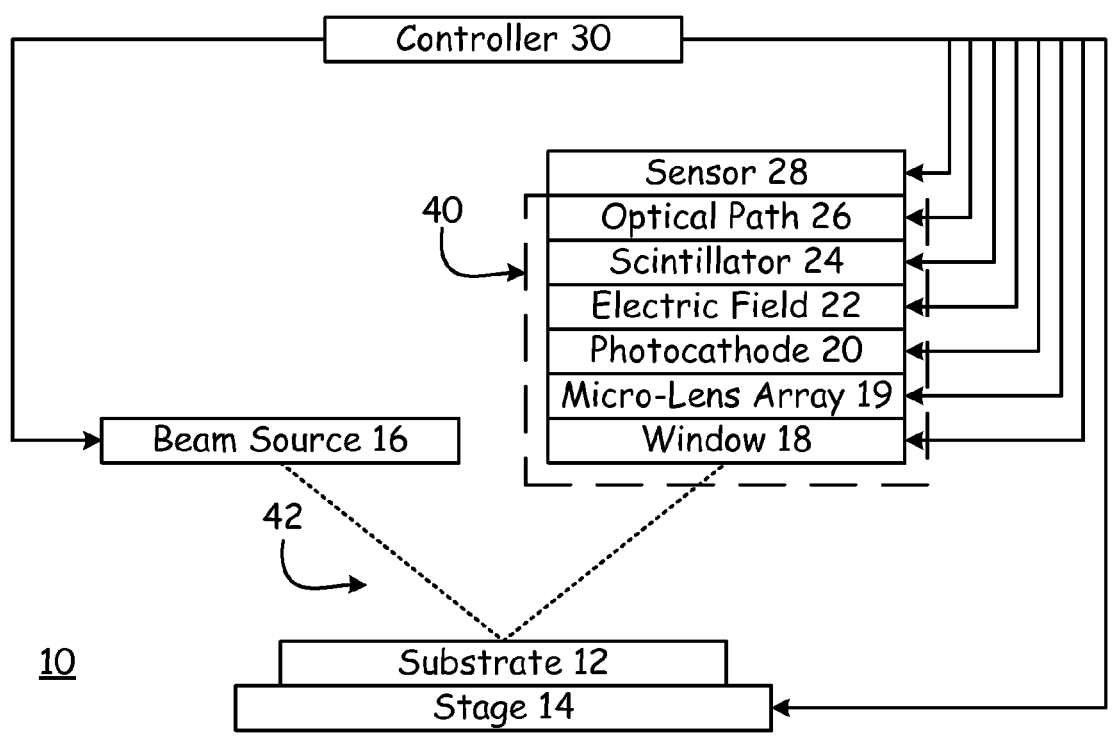
FIG. 1 is a functional block diagram of an inspection system with a signal intensifier module according to an embodiment of the present invention.

With reference now to FIG. 1, there is depicted a functional block diagram of an optical inspection system 10 having an image intensifier module 40 according to an embodiment of the invention. The optical inspection system 10 is used for optically inspecting a substrate 12, which in the embodiment depicted, resides on a movable stage 14. A beam source 16 directs a beam of light 42 toward the substrate 12, which beam of light is reflected off of the substrate 12 and generally toward a sensor 28. An imaging system may be inserted between the substrate 12 and the sensor 28 to create an image of the substrate 12 to be received by the sensor 28. A controller 30 provides control signals to the components, and receives signals from the sensor 28, and provides a representation of the imaged substrate 12, such as on a display.

The beam source 16 could produce a beam 42 having one or more wavelengths within a wide range of wavelengths. For example, the beam source 16 could produce at least one of infrared wavelength, visible wavelengths, and ultraviolet wavelengths. The sensor 28 is matched to the one or more wavelengths produced by the beam source 16. In various embodiments, the sensor 28 is at least one of a charge coupled device, a CMOS device, and a time delay and integration device. Especially in regard to the time delay and integration device, providing a sufficient supply of light tends to be a challenge, and thus such embodiments tend to benefit greatly from the application of the invention.

There is added to the optical inspection system 10 described above, an image intensifier module 40, the purpose of which is to boost the light input that is provided to the sensor 28, and thus generally boost the signal to noise ratio of the inspection system 10. In one embodiment the image intensifier 40 consists of a photocathode 20 and scintillator 24 separated from each other with an electric field 22, which is applied to accelerate photoelectrons from the photocathode 20 into the scintillator 24. These and other elements of the image intensifier module 40 are explained in more detail below.

Figure 2:
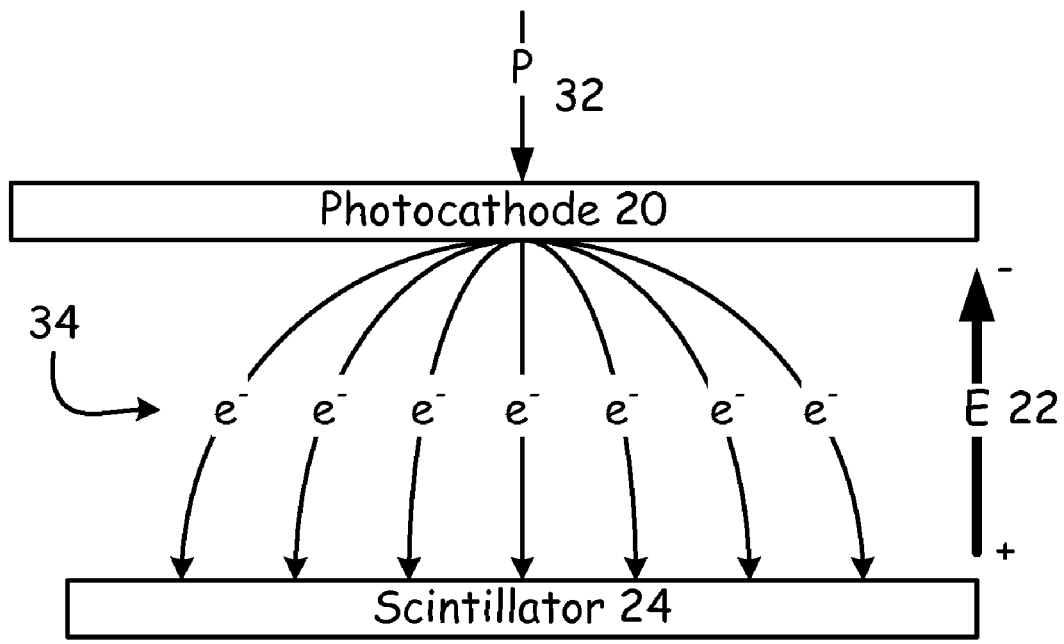
FIG. 2 is a depiction of a proximity focused signal intensifier module according to an embodiment of the present invention.

As depicted in FIG. 2, incoming photons 32 strike the photocathode 20, producing photoelectrons 34, which are accelerated toward and generate a large number of photons within the scintillator 24, thereby creating an optical output that exceeds the input, or in other words, an amplified image. In some embodiments a multichannel plate is positioned between the photocathode 20 and scintillator 24 to provide additional gain.

Figure 3:
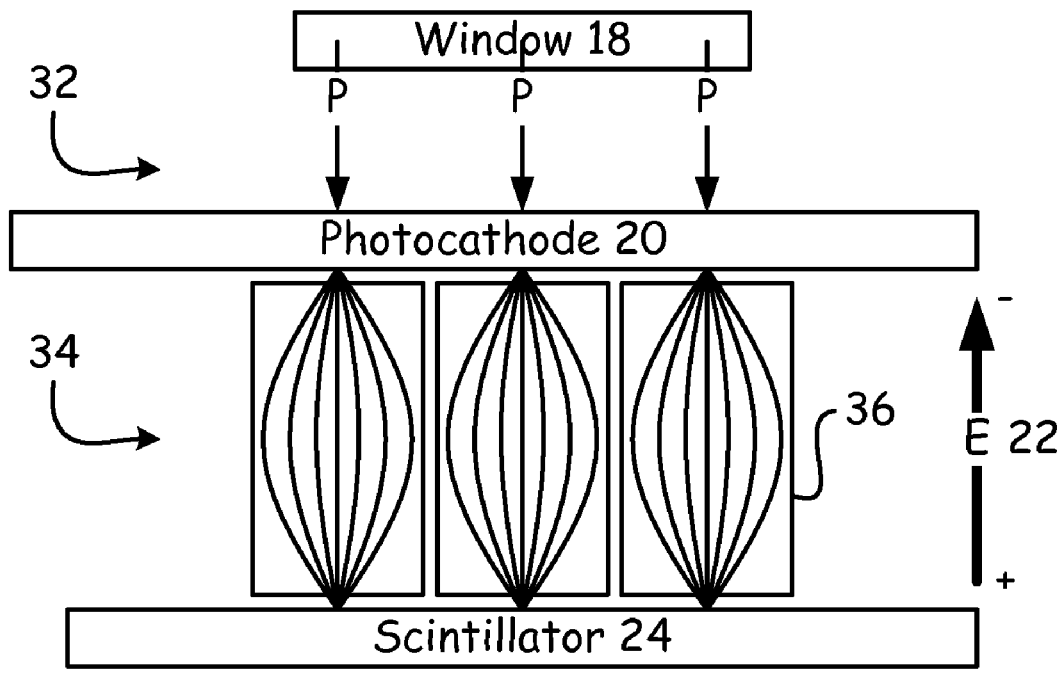
FIG. 3 is a depiction of a magnetically focused signal intensifier module according to an embodiment of the present invention.
Figure 4:
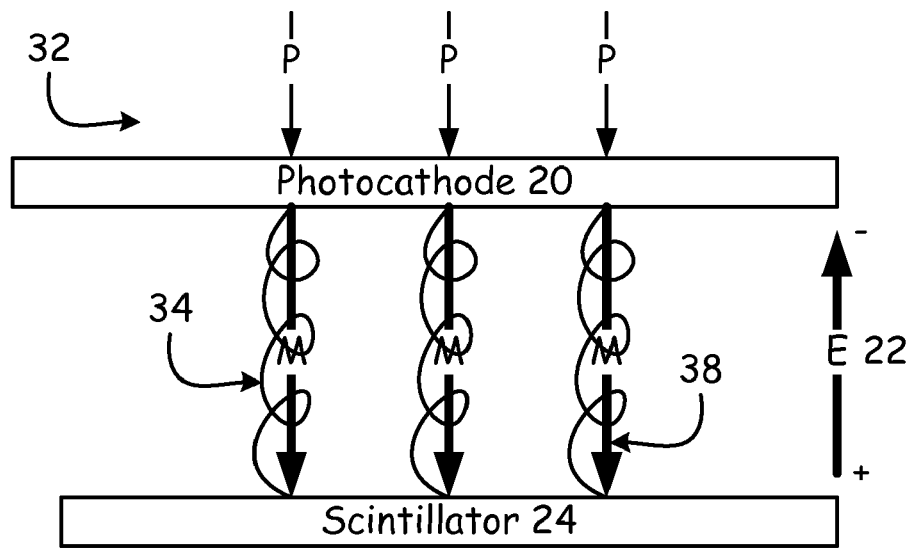
FIG. 4 is a depiction of a magnetically confined signal intensifier module according to an embodiment of the present invention.

To help preserve the spatial information of the image of the substrate 28, the spread of the photoelectrons 34 as they are ejected from the photocathode 20 is controlled in some manner, in some embodiments. This can be accomplished, for example, by (1) a proximity focused intensifier as depicted in FIG. 2, (2) a magnetically focused intensifier as depicted in FIG. 3, and (3) a magnetically confined intensifier as depicted in FIG. 4. These are described in more detail below.

With reference now to FIG. 2, the uniform electric field 22 that accelerates the photoelectrons 34 from the photocathode 20 to the scintillator 24 generally constrains the photoelectrons 34 to a reasonably small region. However, some spatial resolution is lost in this embodiment, as the incoming photon 32 that strikes the photocathode 20 in a single location produces a shower of photoelectrons 34 across a broader surface of the scintillator 24.

With reference now to FIG. 3, one or more uniform magnetic fields are superimposed on the uniform electric field 22, such as by use of one or more magnetic focusing tubes 36. The uniform magnetic fields form an electron image over some distance that is defined by the field strength and other parameters, but as depicted in FIG. 3, can be tuned in one embodiment so as to focus the photoelectron shower 34 that is created by a photon 32 strike to a relatively smaller area on the scintillator 24.

With reference now to FIG. 4, one or more strong magnetic fields 38 are used to focus the photoelectrons 34. In this embodiment, each strike on the photocathode 20 of a photon 32 produces a shower of photoelectrons 34, however, the magnetic fields 38 are strong enough that the Larmor radius of the photoelectrons 34 is small, such that the photoelectrons 34 spiral along the magnetic field lines 38. This produces a spatial signal pattern on the scintillator 24 that corresponds very closely with that of the photons 32 on the photocathode 20.

In some embodiments, the photons ejected from the scintillator 24 are coupled toward the sensor 28, such as by using an optional optical path 26, which is disposed between the scintillator 24 and the sensor 28. In one embodiment the scintillator 24 is coated on or bonded to a fiber optic plate 26. The sensor 28 is then bonded to the air side of the fiber optic plate 26. In other embodiments a relay lens 26 is positioned so that the scintillator 24 is in the object plane of the relay lens 26 and the sensor 28 is in the image plane of the relay lens 26. In some embodiments a demagnifying relay lens is used to limit the impact of the image intensifier point spread function on the resolution of the inspection system 10.

In some embodiments the space between the photocathode 20 and the scintillator 24 of the optical image intensifier module 40 is held at a vacuum, such as in a sealed unit. In such embodiments the elements of the module 40 are generally contained within a casing, and the reflected light beam 42 attains the photocathode 20 through a window 18. The optical path 26 as described above may or may not be disposed within the casing, depending upon the embodiment.

A simplified version of the intensifier module 40 can be constructed without the scintillator 24. Such an embodiment consists of the photocathode 20 and the sensor 28, separated from each other with an electric field 22 that is applied to accelerate photoelectrons 34 from the photocathode 20 to the sensor 28. The methods describe above to preserve the spatial resolution of the image can still be used between the photocathode 20 and the sensor 28.

Figure 5:
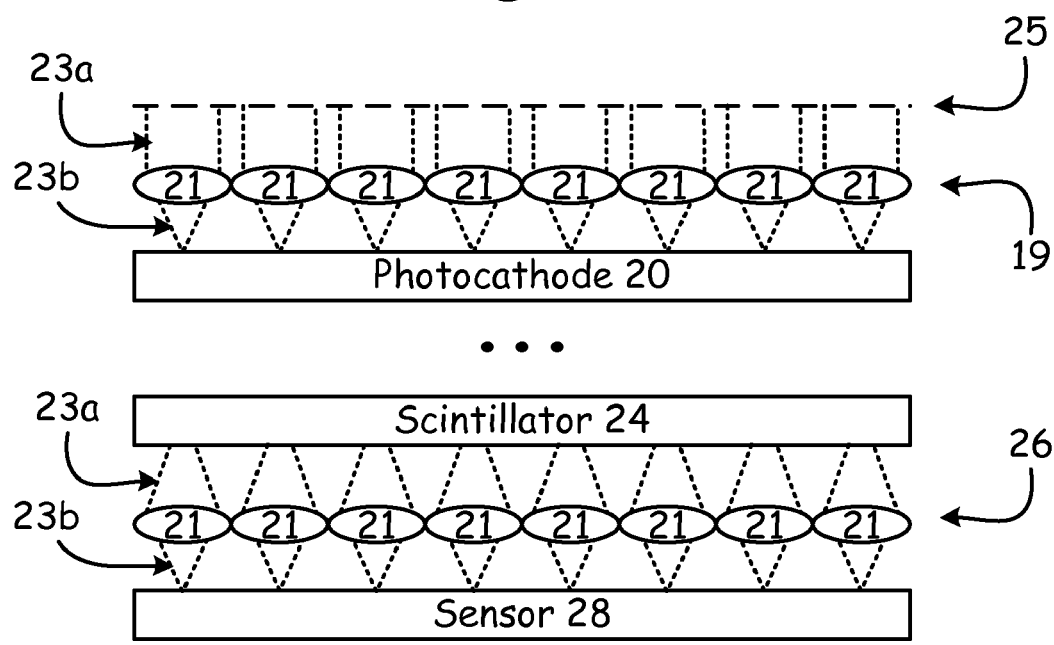
FIG. 5 is a depiction of a micro-lens array, optionally disposed in two different positions, according to an embodiment of the present invention.

In one embodiment, an optional micro-lens array 19 is disposed so as to receive the reflected beam of light 42 prior to it achieving the photocathode 20, as depicted in FIG. 5. The micro-lens array 19 in this embodiment pre-focuses the light 42 from an image plane 25 in rays 23a, through micro-lenses 21 that narrow the rays 23a to rays 23b and onto the photocathode 20, creating smaller light spots on the photocathode 20, thereby relaxing the requirements for electron focusing in the electric field 22. The optical path 26 can also, in one embodiment, include an array of micro-lens 21 to relay the image from the scintillator 24 to the sensor 28.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An optical inspection system for inspecting a substrate, comprising:

a beam source for producing a light beam and directing it toward a surface of the substrate, thereby producing a reflected light beam, an intensifier module comprising, a photocathode for receiving the reflected light beam at a first surface and producing a shower of photoelectrons at a second opposing surface, and an electrical field for receiving the shower of photoelectrons and accelerating the photoelectrons away from the second surface of the photocathode, the intensifier module thereby producing an enhanced output, a sensor for receiving the enhanced output from the intensifier module and for producing electrical signals in response to the enhanced output, and a controller for receiving the electrical signals and producing images of the substrate based at least in part on the electrical signals, the controller also for controlling and coordinating operation of the beam source, the intensifier module, and the sensor.

2. The optical inspection system of claim 1, wherein the intensifier module further comprises a scintillator for receiving the shower of photoelectrons at a first surface and producing photons at a second opposing surface, where the photons are the enhanced output of the intensifier module.

3. The optical inspection system of claim 1, wherein the intensifier module further comprises at least one magnetic focusing tube for receiving the shower of photoelectrons and producing a spatially enhanced shower of photoelectrons, where the spatially enhanced photoelectrons are the enhanced output of the intensifier module.

4. The optical inspection system of claim 1, wherein the intensifier module further comprises a magnetic field for receiving the shower of photoelectrons and producing a spatially enhanced shower of photoelectrons, where the spatially enhanced photoelectrons are the enhanced output of the intensifier module.

5. The optical inspection system of claim 1, wherein the intensifier module further comprises a fiber optic plate for coupling the enhanced output of the intensifier module to the sensor.

6. The optical inspection system of claim 1, wherein the intensifier module further comprises a relay lens for coupling the enhanced output of the intensifier module to the sensor.

7. The optical inspection system of claim 1, wherein the sensor comprises a charge coupled device.

8. The optical inspection system of claim 1, wherein the sensor comprises a CMOS device.

9. The optical inspection system of claim 1, wherein the sensor comprises a time delay and integration device.

10. An optical inspection system for inspecting a substrate, comprising:

a beam source for producing a light beam and directing it toward a surface of the substrate, thereby producing a reflected light beam, an intensifier module comprising, a photocathode for receiving the reflected light beam at a first surface and producing a shower of photoelectrons at a second opposing surface, an electrical field for receiving the shower of photoelectrons and accelerating the photoelectrons away from the second surface of the photocathode, a focusing means existing within the electrical field for receiving the shower of photoelectrons and producing a spatially enhanced shower of photoelectrons, a scintillator for receiving the shower of photoelectrons at a first surface and producing photons at a second opposing surface, and an optical path for receiving the photons and thereby providing an enhanced output, a sensor for receiving the enhanced output from the intensifier module and for producing electrical signals in response to the enhanced output, and a controller for receiving the electrical signals and producing images of the substrate based at least in part on the electrical signals, the controller also for controlling and coordinating operation of the beam source, the intensifier module, and the sensor.

11. The optical inspection system of claim 10, wherein the focusing means comprises at least one magnetic focusing tube.

12. The optical inspection system of claim 10, wherein the focusing means comprises a magnetic field.

13. The optical inspection system of claim 10, wherein the optical path comprises a fiber optic plate.

14. The optical inspection system of claim 10, wherein the optical path comprises a relay lens.

15. The optical inspection system of claim 10, wherein the sensor comprises a charge coupled device.

16. The optical inspection system of claim 10, wherein the sensor comprises a CMOS device.

17. The optical inspection system of claim 10, wherein the sensor comprises a time delay and integration device.

18. An optical inspection system for inspecting a substrate, comprising:

a beam source for producing a light beam and directing it toward a surface of the substrate, thereby producing a reflected light beam, an intensifier module comprising, a photocathode for receiving the reflected light beam at a first surface and producing a shower of photoelectrons at a second opposing surface, an electrical field for receiving the shower of photoelectrons and accelerating the photoelectrons away from the second surface of the photocathode, a focusing means existing within the electrical field for receiving the shower of photoelectrons and producing a spatially enhanced shower of photoelectrons, where the focusing means comprises at least one of a magnetic focusing tube and a magnetic field, a scintillator for receiving the shower of photoelectrons at a first surface and producing photons at a second opposing surface, and an optical path for receiving the photons and thereby providing an enhanced output, where the optical path comprises at least one of a fiber optic plate and a relay lens, a sensor for receiving the enhanced output from the intensifier module and for producing electrical signals in response to the enhanced output, where the sensor comprises at least one of a charge coupled device, a CMOS device, and a time delay and integration device, and a controller for receiving the electrical signals and producing images of the substrate based at least in part on the electrical signals, the controller also for controlling and coordinating operation of the beam source, the intensifier module, and the sensor.

* * * * *